(12) United States Patent
Ingram et al.

(10) Patent No.: US 7,780,038 B2
(45) Date of Patent: Aug. 24, 2010

(54) DISPENSING APPARATUS WITH DOSAGE COUNTER

(75) Inventors: Simon Ingram, Northampton (GB); Nick Campling, Cambridgeshire (GB); Duncan Bradley, Cambridgeshire (GB)

(73) Assignee: Consort Medical plc, Hertfordshire (GB)

( * ) Notice: Subject to any disclaimer, the term of this patent is extended or adjusted under 35 U.S.C. 154(b) by 611 days.

(21) Appl. No.: 11/597,354

(22) PCT Filed: May 23, 2005

(86) PCT No.: PCT/GB2005/002007

§ 371 (c)(1), (2), (4) Date: Sep. 6, 2007

(87) PCT Pub. No.: WO2005/113044

PCT Pub. Date: Dec. 1, 2005

(65) Prior Publication Data
US 2008/0135575 A1    Jun. 12, 2008

(30) Foreign Application Priority Data
May 21, 2004    (GB) ................... 0411384.1

(51) Int. Cl.
*B67D 7/22* (2010.01)
(52) U.S. Cl. .................. 222/36; 128/205.23
(58) Field of Classification Search ............ 222/26–49, 222/23; 128/205.23, 200.23, 200.14
See application file for complete search history.

(56) References Cited

U.S. PATENT DOCUMENTS

| | | | |
|---|---|---|---|
| 3,178,110 A | 4/1965 | Knecht et al. | |
| 4,563,574 A | 1/1986 | Dreyer et al. | |
| 5,565,861 A | 10/1996 | Mettler et al. | |
| 5,808,337 A | 9/1998 | Weimer et al. | |
| 6,234,168 B1 * | 5/2001 | Bruna | 128/203.12 |
| 7,322,352 B2 * | 1/2008 | Minshull et al. | 128/203.15 |
| 7,448,342 B2 * | 11/2008 | Von Schuckmann | 116/307 |
| 7,464,708 B2 * | 12/2008 | Marx | 128/205.23 |
| 7,571,726 B2 * | 8/2009 | Parker | 128/204.26 |
| 7,587,988 B2 * | 9/2009 | Bowman et al. | 116/307 |
| 2004/0065326 A1 * | 4/2004 | MacMichael et al. | 128/205.23 |
| 2004/0149773 A1 | 8/2004 | Ouyang et al. | |

(Continued)

FOREIGN PATENT DOCUMENTS

CA    2 392 466 A1    6/1997

(Continued)

OTHER PUBLICATIONS

Combined Search and Examination Report dated Aug. 26, 2004 corresponding to GB0411384.1.

*Primary Examiner*—Lien T Ngo
(74) *Attorney, Agent, or Firm*—Smith, Gambrell & Russell, LLP (57) ABSTRACT

A dispensing apparatus (1) comprising a housing containing a dosage counter comprising at least two annular members (11, 13) and a cog (12), each being mounted rotationally. The housing is suitable for receiving, in use, a container (1) containing a product for dispensation. Each actuation of the apparatus causes the first annular member to incrementally rotate which, after a predetermined number of actuations of the apparatus, causes the cog to rotate, the rotation of the cog causing the second annular member to incrementally rotate.

39 Claims, 9 Drawing Sheets

U.S. PATENT DOCUMENTS

| | | | |
|---|---|---|---|
| 2004/0211420 A1 | 10/2004 | Minshull et al. | |
| 2007/0181120 A1* | 8/2007 | Wright et al. | 128/200.23 |
| 2007/0246042 A1* | 10/2007 | Purkins et al. | 128/200.14 |
| 2008/0265198 A1* | 10/2008 | Warby | 251/214 |
| 2009/0139516 A1 | 6/2009 | Augustyn et al. | |

FOREIGN PATENT DOCUMENTS

| | | |
|---|---|---|
| DE | 805 817 | 5/1951 |
| DE | 1237 820 | 3/1967 |
| DE | 27 51 045 | 7/1978 |
| WO | 02/067844 | 9/2002 |
| WO | WO 2004/001664 A1 | 12/2003 |
| WO | WO 2004/026380 | 4/2004 |
| WO | 2005/079727 | 9/2005 |

* cited by examiner

DISPENSING APPARATUS WITH DOSAGE COUNTER

This invention relates to dispensing apparatus having integral dosage counting devices which require an axial force for actuation. In particular, the invention relates to dispensing apparatus having a dosage counter.

It has been recognised that there is a need to provide accurate information to a user of a dose-dispensing delivery apparatus concerning the number of doses delivered from, or remaining in, the dispensing apparatus. Without such information, there is a danger that a user will forget how many doses have been delivered and hence take a greater or fewer number of doses than is required. There is also a danger that a user may be unaware that the dispensing apparatus is empty or close to empty. This is especially dangerous where the dispensing apparatus is for use in delivering medicinal compounds for the treatment of chronic or acute symptoms, for example, as in the case of a pressurised metered dose inhaler used for treating asthmatic reactions.

A number of devices have been proposed to count the number of doses delivered or remaining in a delivery apparatus. WO95/08484 teaches a dose counting device for use with an aerosol medication dispenser. The device works by translating a non-rotative force on an outer cover into a rotation of an indicator wheel by use of a set of flexible pawls engaged with a set of teeth. The pawls depress and thereby extend circumferentially when the applied force forces them to effect a rotation of the teeth. This device has, however, been found to have disadvantages. The reliability of operation of the medication dispenser and the pawls, for example. If the pawls are too stiff relative to the internal spring bias then the medication dispenser may dispense a dose before the pawls flex sufficiently to rotate the indicator wheel; a dose would be delivered without the counter registering it. Alternatively, if the pawls are too flexible relative to the internal spring bias then the pawls may flex sufficiently to rotate the indicator wheel before the medication dispenser has dispensed a dose; a dose would be registered by the counter but not actually delivered.

EP1065477 describes a dose dispenser with a device for counting the dispensed doses, wherein the dispenser comprises a base body, an operating body superimposed on the base body, a first discoidal body housed in and rotable within the operating body, and wherein flexible tangs projecting on the first discoidal body cause the first discoidal body to rotate one step each time the operating body is moved axially relative to the base body.

The present invention seeks to provide dispensing apparatus having integral dosage counting devices which overcome at least some of the associated disadvantages of the prior art.

Accordingly, in a first aspect, the invention provides a dispensing apparatus comprising a housing containing a dosage counter comprising at least two annular members and a cog, each mounted rotationally, the housing being suitable for receiving, in use, a container containing a product for dispensation, whereupon each actuation of the apparatus causes the first annular member to incrementally rotate which, after a predetermined number of actuations of the apparatus, causes the cog to rotate, the rotation of the cog causing the second annular member to incrementally rotate.

In use, a longitudinal actuation force applied to the container is converted to a rotational force applied to the first annular member by way of co-operating formations having angled abutment surfaces.

Preferably, the first annular member is provided with angled abutment surfaces.

The dispensing apparatus further comprises a cap or sleeve, for surrounding at least part of a container locatable in the dispensing apparatus. The cap or sleeve is provided with angled abutment surfaces.

Most preferably, the first annular member, and/or the cap or sleeve is/are provided with one or more sets of angled abutment surfaces at different diameters.

In use, respective sets of angled abutment surfaces of the first annular member, and the cap or sleeve co-operate to provide an incremental rotation of the first annular member upon a longitudinal actuation of the sleeve or cap. In particular, a first set of co-operating portions of the first annular member, and the sleeve or cap co-operate to provide a partial-incremental rotation of the annular member upon a down-stroke longitudinal actuation of the dispensing apparatus. A second set of co-operating portions of the first annular member, and the sleeve or cap co-operate to provide a second and final partial-incremental rotation of the first annular member upon a reciprocal up-stroke longitudinal actuation of the dispensing apparatus.

The first annular member may be provided with means for affecting rotation of the cog, such as a notch or protrusion positioned on an outer edge of the first annular member. The notch or protrusion is capable of interacting with a correspondingly-shaped portion of the cog.

When the rotation means of the first annular member is a notch, the cog is turned by way of a tooth catching the notch of the first annular member as the member rotates upon actuation of the apparatus. Similarly, when the rotation means of the first annular member is a protrusion, the cog has a correspondingly-shaped notch with which to affect the desired rotation of the cog.

The first annular member has three rotation means positioned on its outer edge, at least ten increments of rotation apart.

Preferably, each respective part of the cog which interacts with the first and second annular member has a different number of teeth. More preferably, the ratio of teeth on respective parts of the cog which interact with the first and second annular member is 1:2.

The axis of rotation of the cog may be positioned offset from the axes of rotation of both the first and second annular members.

The cog may be made of resilient material and/or resiliently positioned against an outer edge of the first annular member.

Preferably, the first and second annular members are provided with one or more sets of markings indicative of the amount or number of doses of product dispensed from, or remaining in, a container received within the apparatus. In particular, the sets of markings may be numbering or variations of colour and/or tone.

As a preference, numbering on the first annular member ranges from 0 to 9 and that of the second annular member from 00 to 20, so that when both are seen in combination, a three-figure number is shown.

Upon actuation of the apparatus, the numbering is caused to decrease or augment by a value of one.

Preferably, the second annular member is provided with an extended portion which is positioned on the second annular member so as to cover the markings of the first annular member when a container locatable in the housing is empty.

Optionally, the dispensing apparatus may further comprise means for locking-out operation of a container located in the housing.

As a preference, the dispensing apparatus is provided with a mouthpiece which is detachable from the housing.

Additionally, a portion of the sleeve or cap and a portion of the housing may be adapted to provide resistance to actuation of the dispensing apparatus. The portion of the sleeve or cap is a resilient member and the portion of the housing is a static abutment surface which, during use, is temporarily abutable by the portion of the sleeve or cap.

The dispensing apparatus may further comprise third and subsequent annular members, a further cog being provided for each additional annular member, whereby a predetermined number of rotations of the previous annular member causes an incremental rotation of the subsequent member.

The cog of the first aspect of the invention comprises a hub, with a pivot hole situated in the centre thereof, and a plurality of teeth outwardly-extending from the centre of the cog, the cog being rotatable about a longitudinal axis through the hole, wherein one or more teeth have a reduced-height in the direction of the longitudinal axis in that upper and lower edges of the tooth are not inline with both upper and lower faces of the cog.

Preferably, the one or more teeth having a reduced height are half the height of other teeth and are interspaced between each pair of non-reduced-height teeth.

Preferably, also, the reduced-height teeth are positioned at either an upper or lower edge of the cog.

The invention also includes dispensing apparatus substantially as herein described, with reference to, and as shown in, the accompanying drawings.

Portions of the one or more teeth may be separated by a non-toothed spacer, such that, in use, a first end of the cog, including one or more teeth of reduced height, may interact with the first annular member and a second end of the cog, which is not provided with one or more teeth of reduced height, may interact with the second annular member. The one or more teeth having reduced height are half the height of the non-reduced-height teeth, which non-reduced-height teeth extend from the spacer to the face of the first end of the cog. Preferably, the cog comprises a reduced-height tooth interspaced between each pair of non-reduced-height teeth.

The dispensing apparatus may further comprise a container located in the housing of the dispensing apparatus. The container is, preferably, pressurised. Preferably, the annular members are located around the container. The container is locatable within the dispensing apparatus, such that the container is locatable within the holes/apertures of the at least two annular members. In other words, the annular members surround at least part of the container when the container is loaded within the dispensing apparatus.

According to a second aspect of the present invention, there is provided a combination comprising an apparatus according to the first aspect of the present invention and a container located in the housing of the apparatus.

Preferably, the container located in the apparatus is pressurised.

The invention also includes combinations substantially as herein described, with reference to the accompanying drawings.

In a third aspect of the present invention, there is provided a cog comprising a hub, with a pivot hole situated in the centre thereof, and a plurality of teeth outwardly-extending from the centre of the cog, the cog being rotatable about a longitudinal axis through the hole, wherein one or more teeth have a reduced-height in the direction of the longitudinal axis in that upper and lower edges of the tooth are not inline with both upper and lower faces of the cog.

Preferably, the one or more teeth having a reduced height are half the height of the other teeth and are interspaced between each pair of non-reduced-height teeth.

Preferably, also, the reduced-height teeth are positioned at either an upper or lower edge of the cog and are made of a resilient material.

The invention also includes cogs substantially as herein described, with reference to the accompanying drawings. The dispensing apparatus may be a pharmaceutical dispensing device, such as, for example, a pulmonary, nasal, or sublingual delivery device. A preferred use of the dispensing apparatus is as a pharmaceutical metered dose aerosol inhaler device. The term pharmaceutical, as used herein, is intended to encompass any pharmaceutical, compound, composition, medicament, agent or product which can be delivered or administered to a human being or animal, for example pharmaceuticals, drugs, biological and medicinal products. Examples include antiallergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl) protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bircarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylamine, triethylamine, 1-amino-2-propanol-amino-2-(hydroxymethyl)propane-1,3-diol, and 1-(3,4-dihydroxyphenyl)-2 isopropylaminoethanol.

The pharmaceutical will typically be one which is suitable for inhalation and may be provided in any suitable form for this purpose, for example as a solution or powder suspension in a solvent or carrier liquid, for example ethanol, or isopropyl alcohol. Typical propellants are HFA134a, HFA227 and dimethyl ether.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. As will be appreciated, the pharmaceutical may comprise of one or more active ingredients, an example of which is flutiform, and may optionally be provided together with a suitable carrier, for example a liquid carrier. One or more surfactants may be included if desired.

Rigid components of the dispensing apparatus may be formed from, for example, from polyester, nylon, acetal or similar.

Actuation of a dispensing apparatus involves, typically, depression of the valve stem of the container—which provides dispensation of product—followed by a reciprocal resilient movement of the valve stem—which resets the metering valve of the container ready for further dispensations.

In order that the invention may be fully disclosed, an embodiment will now be described, by way of example, with reference to the accompanying drawings, in which.

Figure 1:
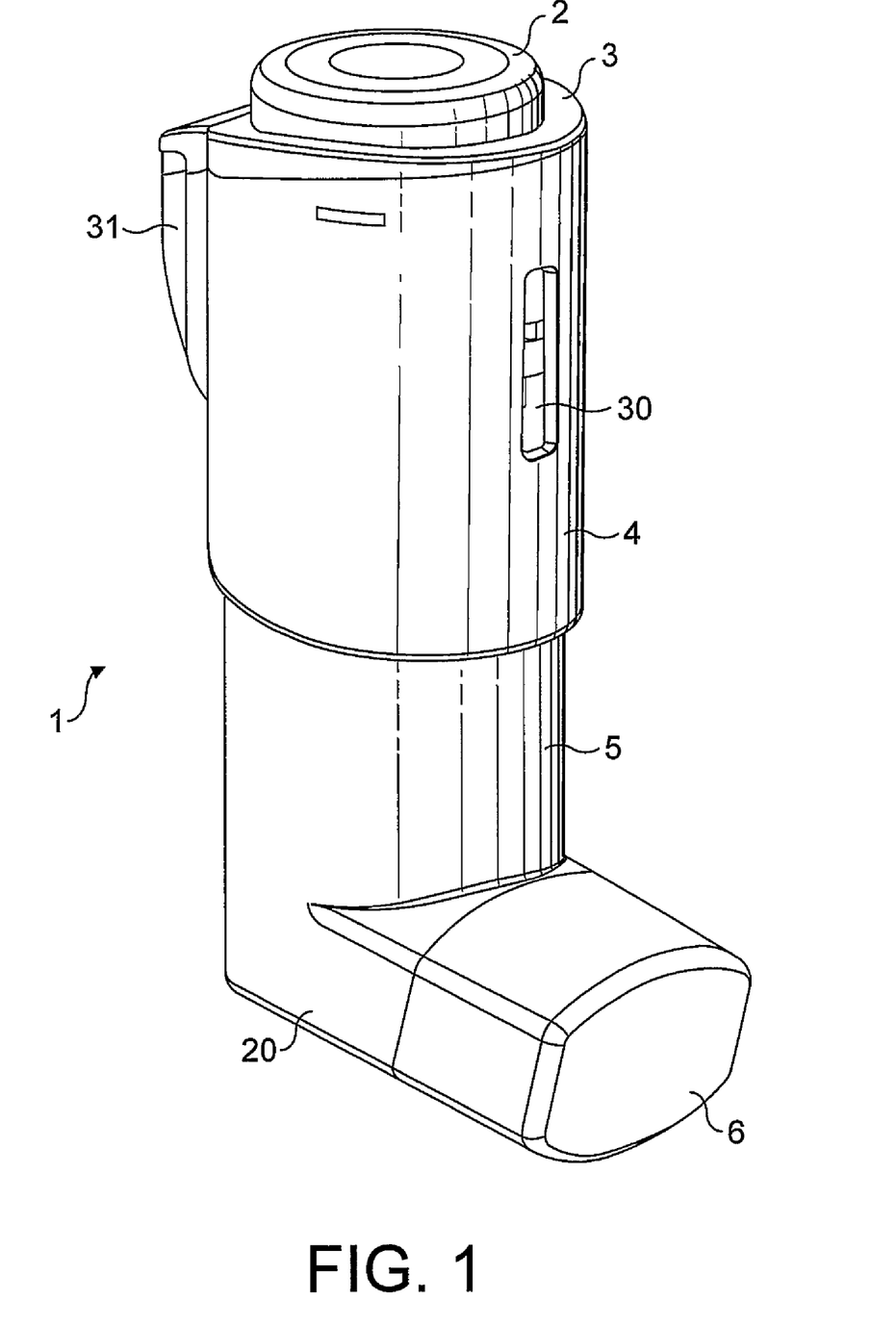
FIG. 1 is a perspective view of a dispensing apparatus according to in accordance with the present invention.

FIG. 1 shows a dispensing apparatus, indicated generally at 1, having a cap 2, a fixing collar 3, a counter body 4, a main body 5 and a dust cap 6.

Figure 2:
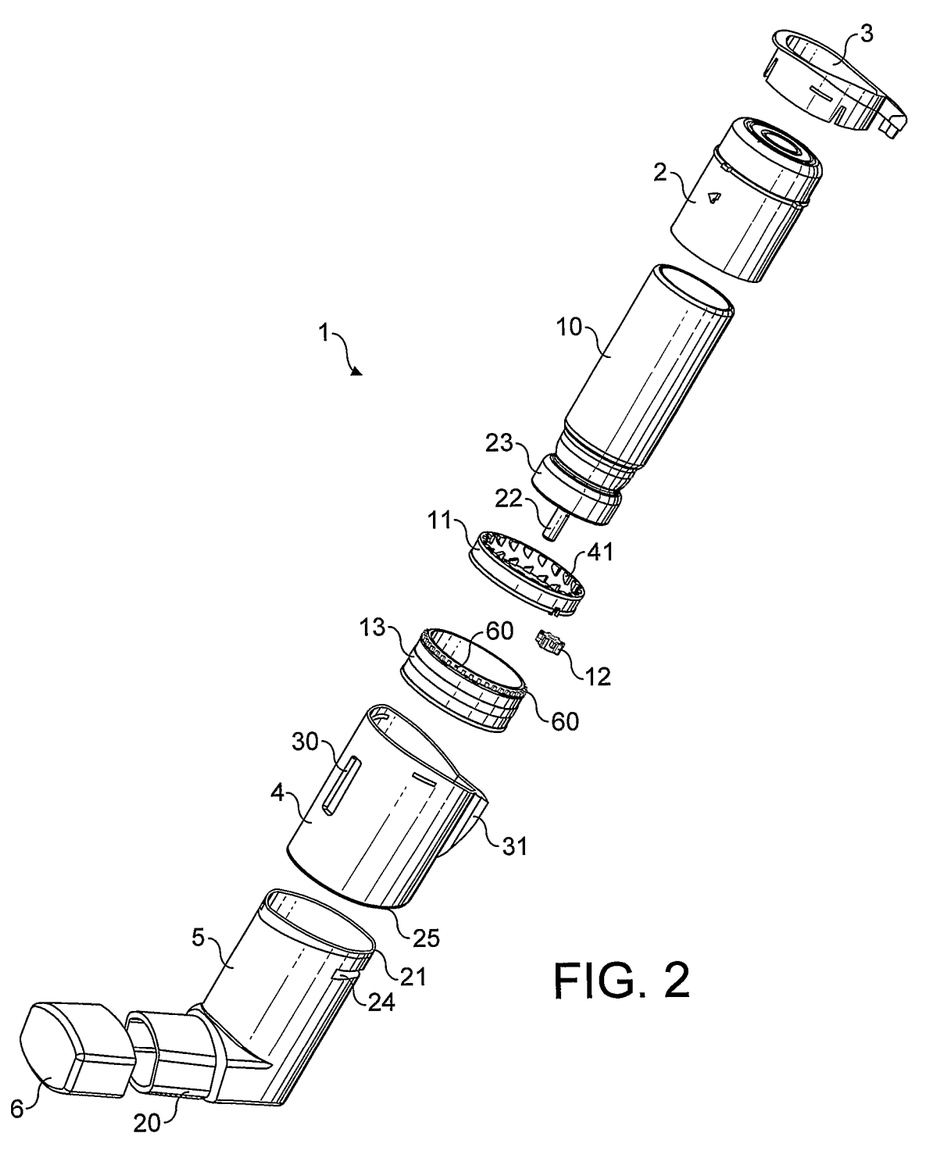
FIG. 2 is an exploded view of the dispensing apparatus of FIG. 1, together with a container.
Figure 3:
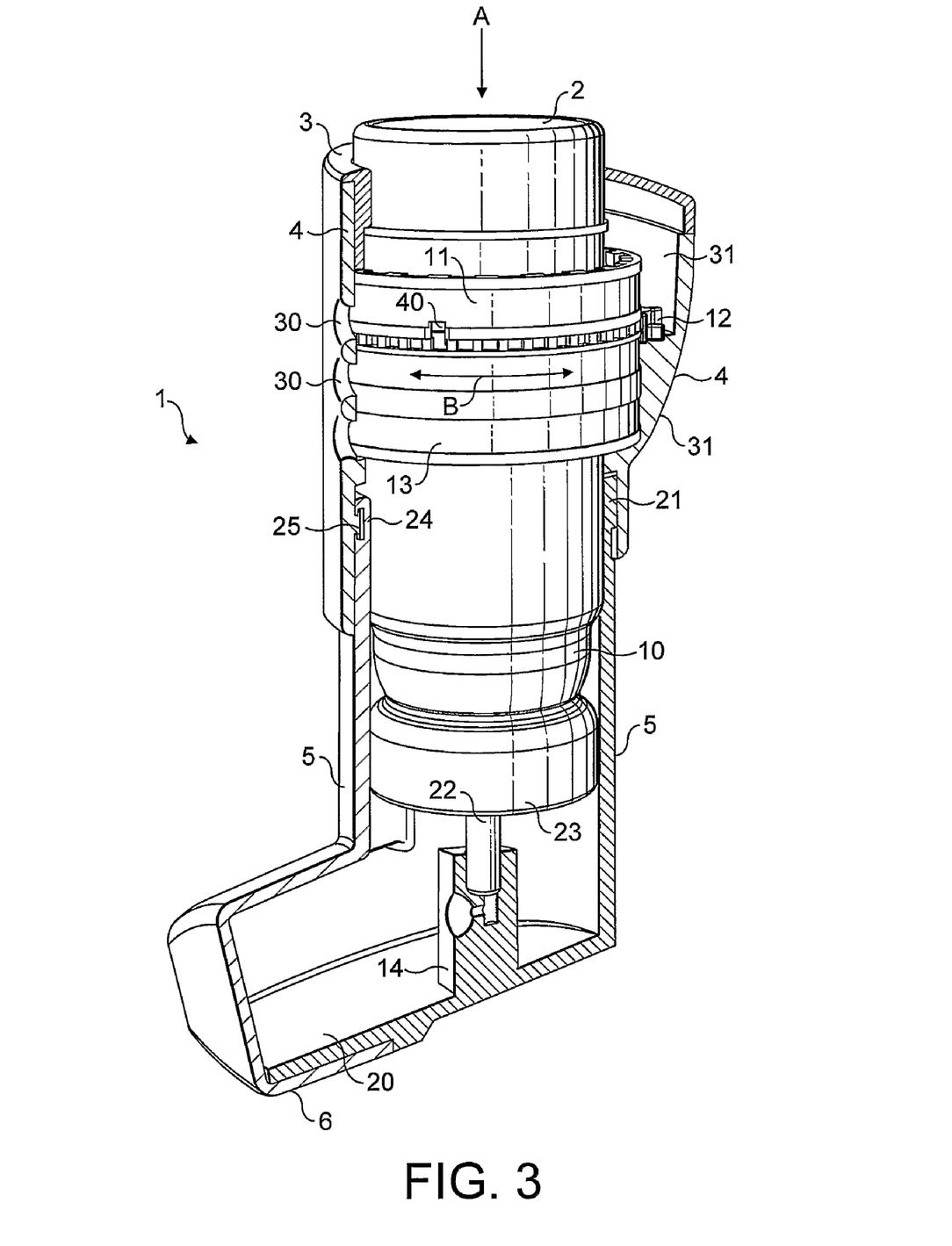
FIG. 3 is a partial cross-sectional view of the apparatus of FIG. 1.

FIGS. 2 and 3 show internal features of the dispensing apparatus of FIG. 1, wherein the apparatus comprises, a first number ring 11 (first annular member), a cog 12, a second number ring 13 (second annular member) and a valve stem receiving block 14. A separate container of product 10 is also shown.

Referring to FIGS. 1 to 5, the main body 5, which is substantially cylindrical, is provided with an elongate mouthpiece 20 at a lower end—in relation to the dispensing apparatus,—the end of which may be covered by the dust cap 6, and an open end 21 situated at the other and relative upper end of the main body 5 remote from the mouthpiece 20. The valve stem receiving block 14 is positioned within the main body 5 so that it may receive a valve stem 22 of the container 10—which may be inserted into position through the open end 21—and is positioned so that, when the apparatus 1 is actuated, the product is dispensed through the mouthpiece 20 and out of the dispensing apparatus. The container 10 also comprises a metering valve which is retained by means of a ferrule 23. A valve stem 22 extends from the metering valve so that metered doses of product can be dispensed therethrough on actuation of the valve mechanism. The main body 5 also comprises a first functional part of a twist-fit arrangement 24 located adjacent the open end 21.

Figure 6:
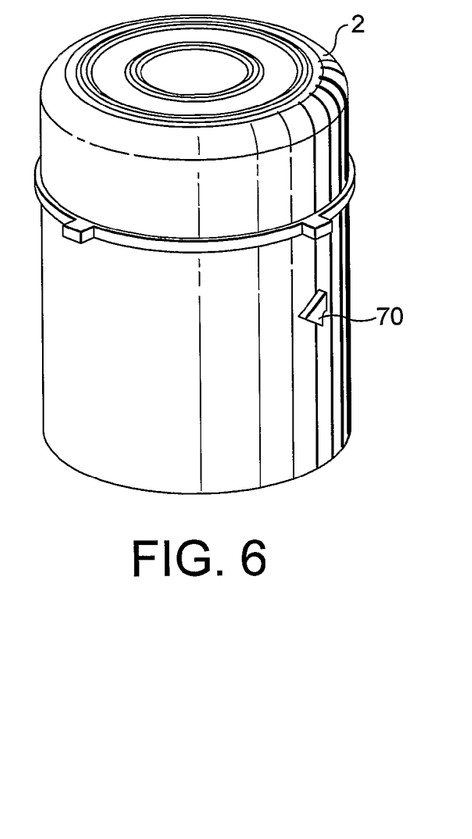
FIG. 6 is a perspective view of the top and one side of a cap of the dispensing apparatus of FIG. 1.
Figure 7:
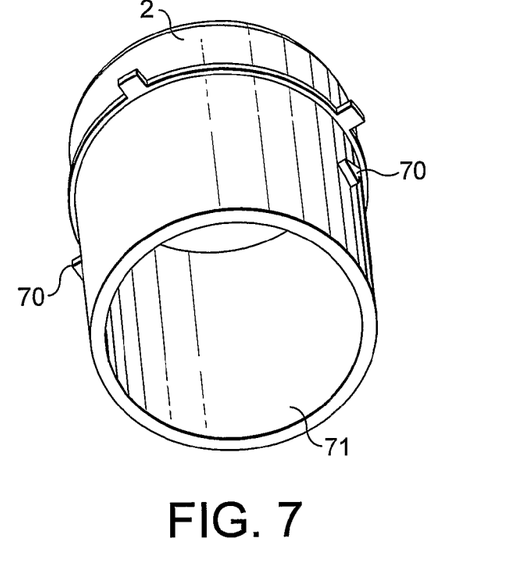
FIG. 7 is a perspective view of the bottom and one side of a cap of the dispensing apparatus of FIG. 1.
Figure 8:
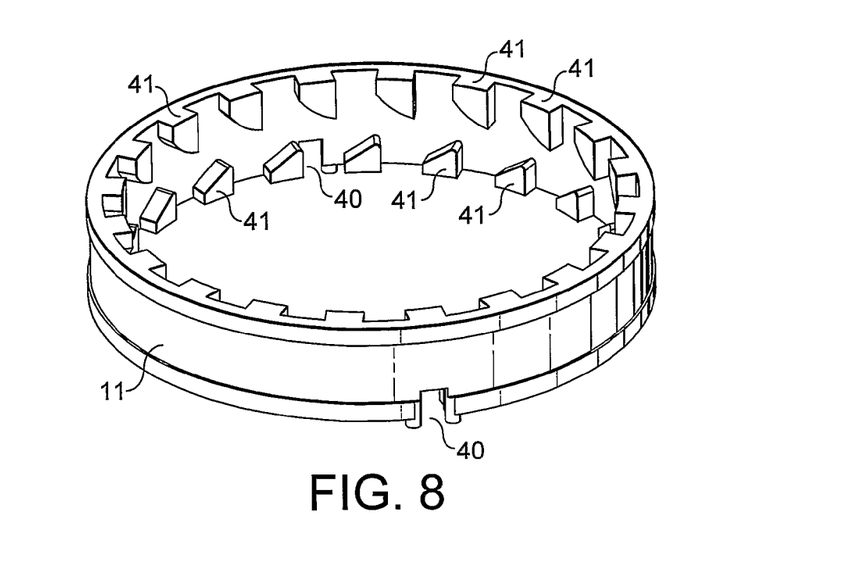
FIG. 8 is a perspective view of a first number ring of the dispensing apparatus of FIG. 1.
Figure 9:
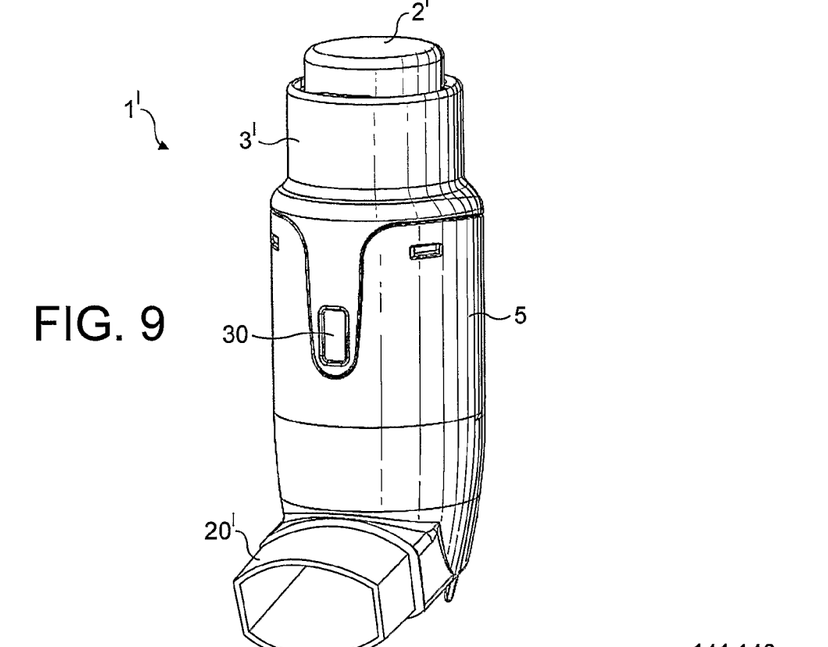
FIG. 9 is a perspective view of an alternative embodiment of dispensing apparatus according to the present invention.

The counter body 4, which is substantially cylindrical, further comprises one or more apertures 30 through the side of the counter body 4 and an enlarged portion 31, and is open at both relative upper and lower ends. The enlarged portion 31, situated at the upper end thereof,—in relation to the dispensing apparatus—houses the cog 12 and the first and second number rings 11,13. The axis of the cog 12 is offset from the axes of the numbered rings 11,13 so that the cog 12 can interact with both number rings 11,13 which are housed in the substantially cylindrical part of the counter body 4 without impeding axial movement of the container 10. The cap 2 is positioned at the upper end of the counter body 4 and overlies an upper end of the container 10. The cap 2 is axially slidable within the counter body 4 so that it may interact with the first number ring 11. The cap 2 and first number ring 11 have co-operating formations 41 having angled abutment surfaces which can interact with each other upon actuation of the apparatus 1. FIGS. 6 to 8 show in more detail the co-operating formations. In particular, the cap 2, which is substantially cylindrical, is provided with one or more substantially triangular teeth 70 (angled abutment surfaces), equally spaced around the outer circumference of the cap 2 and is open at a lower end 71, so that an end of a container 10 may be inserted therein.

As shown in FIG. 3, a container 10 loaded in the dispensing apparatus 1 is slidable through holes/apertures of the number rings 11,13 when the apparatus is actuated.

The first number ring 11 comprises at least one notch 40 positioned on the outer edge thereof and angled abutment surfaces 41 which can co-operate with the corresponding substantially triangular teeth 70 of the cap 2. The first number ring 11 is also provided with a set of numbering from 0 to 9 for each notch 40, so that after the ninth actuation of the apparatus 1, the notch 40 is in position to interact with the cog 12. In a preferred embodiment, the number ring 11 will have three notches 40 and, so, will have three sets of numbering from 0 to 9.

The cap 2, the cog 12 and the first and second number rings 11,13 are held within the counter body 4 by a fixing collar 3, which forms a push-fit connection with the upper end of the counter body 4. The counter body 4 also comprises a second functional part of a twist-fit arrangement 25 situated internally and adjacent the lower-end of the counter body.

Figure 4:
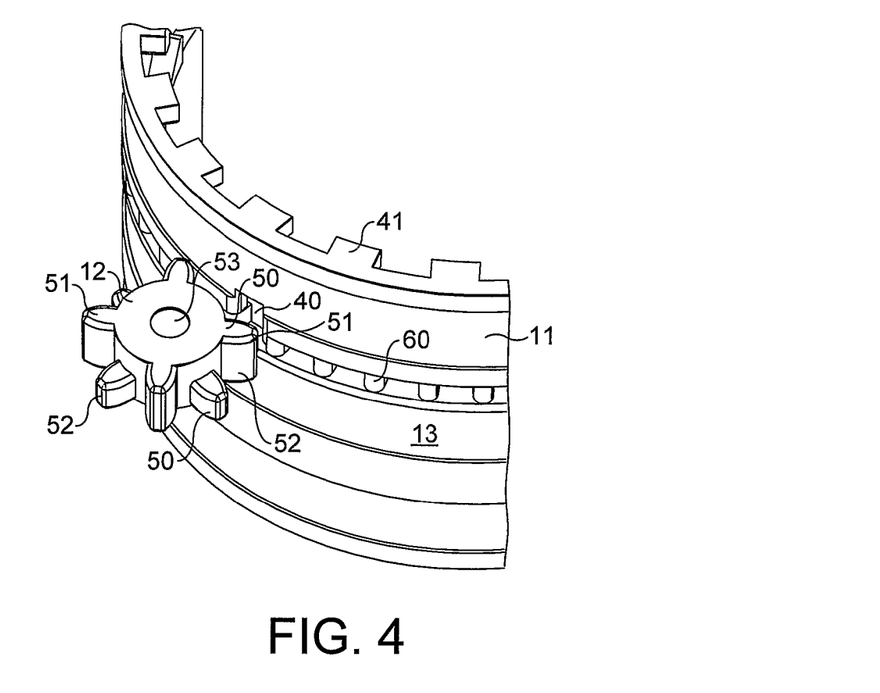
FIG. 4 shows first and second number rings and a cog of the dispensing apparatus of FIG. 1.
Figure 5:
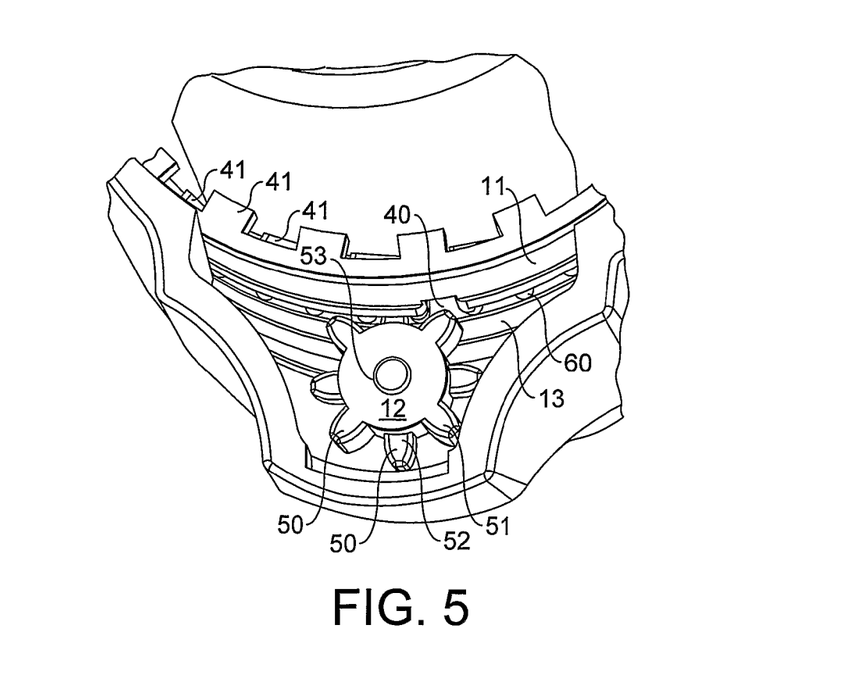
FIG. 5 is a partial plan view of the dispensing apparatus of FIG. 1.

The cog 12, as more clearly shown in FIGS. 4 and 5, is provided with a hole 53 situated in the centre thereof, and a plurality of teeth 50 outwardly-extending from the centre of the cog 12. The cog 12 is rotatably mounted about a longitudinal axis through the hole 53. Each alternate tooth 50 has a reduced-height in the direction of the longitudinal axis in that upper and lower edges of the teeth 50 are not inline with both upper and lower faces of the cog 12. The cog 12 is, therefore, arranged so that when there are eight teeth 50 on a lower row of teeth 52, an upper row of teeth 51 has only four teeth 50.

The upper and lower rows of teeth 51,52 are arranged such that they interact only with the first and second number rings 11,13, respectively. In an alternative, the upper and lower teeth 50 may be misaligned in the form of two distinct rows, or, indeed, the upper teeth 50 may be extensions of some of the lower teeth 50, as shown in FIGS. 4 and 5.

The second number ring 13 is provided with a plurality of teeth 60, positioned adjacent an upper edge of the number ring 13, and numbering on the outside of the number ring 13. The numbering ranges from 00 to 20, the distance between each number corresponding to the distance between two teeth 60.

The apertures 30 are positioned such that numbering on the outside of the number rings 11,13 can be seen by a user. In an alternative embodiment, only numbering on the second number ring 13 is visible by a user through the apertures 30. In a further alternative, numbering on the outside of the number rings 11,13 may be substituted for markings, such as variations of colours and/or tone, or, even, indicators such as Full, ¾, ½, ¼, or Empty, for example.

The main body 5 and the counter body 4 are connected together by means of a twist-fit arrangement using the first and second functional parts 24,25 which hold the two bodies 4,5 together securely. The dust cap 6 is secured to the mouthpiece 20 by means of a push-fit arrangement.

Referring to all the FIGS. 1 to 8, in use, a container 10 can be loaded into position within the apparatus 1 by twisting apart the counter body 4 and the main body 5 and pushing a container 10, valve stem 22 first, into the opening of the main body 21, and positioning the valve stem 22 into the valve stem receiving block 14. Such loading inserts the container 10 through central holes/apertures of number rings 11,13 and, when loaded, the number rings 11,13 are located around the container 10.

Actuation of the apparatus 1, by depression of the cap 2 in the direction of Arrow A, causes an amount of product to be dispensed from the container 10 by an opposite reaction force from the valve stem receiving block 14 acting on the valve stem 22, which is inwardly retracted relative to the remainder of the metering valve such that an amount of product is dispensed from the valve stem 22 through the valve stem receiving block 14, from where it is dispensed as an aerosol through the mouthpiece 20 and inhaled by a user inhaling on the mouthpiece 20. Release of the cap 2 causes the cap 2 and the container 10 to return to its starting position, owing to the internal spring bias of the metering valve, ready for subsequent dispensing.

Each actuation of the apparatus 1 causes the first number ring 11 to incrementally rotate in only one of either direction of Arrow B continuously owing to engagement of the co-operating formations, having angled abutment surfaces, between the cap 2 and the first number ring 11.

Every ten actuations of the apparatus 1 cause a notch 40 to pass the cog 12, the effect of this being that a tooth 50 of the upper row of teeth 51 is caught in the notch 40 as it rotates, this rotation causes a corresponding opposite rotation of the cog 12, the second number ring 13 being caused to rotate in the same direction as the first number ring 11. Therefore, it can be seen that every actuation of the apparatus causes the value of the numbering visible through the one or more apertures 30 to be decreased or augmented by a value of one.

FIGS. 9 to 16 show an alternative embodiment of dispensing apparatus according to the present invention. In relation to this alternative embodiment, like references will be used to describe like items, where necessary. However, it is intended to predominantly describe additional or alternative features, although this alternative embodiment may include many of the features of the embodiment discussed or shown in relation to FIGS. 1 to 8.

The alternative embodiment is indicated generally at 1'. The dispensing apparatus 1' has a cap 2', fixing collar 3', a main body 5' and a detachable mouthpiece 20'. The dispensing apparatus is also provided with first and second number rings 11,13, a cog 12' and a sleeve 100, as shown in FIG. 10.

In this embodiment, only one body portion (main body 5') is provided. The main body 5' houses the number rings 11,13, cog 12' and container 10 on assembly. As shown in more detail in FIG. 15, the number rings 11,13 may rest upon internal projections 110 of the main body 5'. Such internal projections 110 provide up-facing surfaces 111 upon which the second number ring 13 may rest and rotate, during use. The first number ring 11 rests and rotates, during use, on top of the second number ring 13. The cog 12 is rotatably mounted within the main body 5' on a cylindrical portion 112 and interacts with both first and second number rings 11,13. The internal projections 110, of which there are typically four, also interact with the sleeve 100. In addition, the main body 5' is provided with a static abutment surface 113 which may interact with at least part of the sleeve 100, as discussed below. The main body 5' is also provided with a hollow elongate portion 121 into which the valve stem 22 of a loaded container 10 passes. This elongate portion 121 provides a seal with the valve stem 22 and an abutment against which the valve stem is pressed during actuation of the dispensing apparatus. The elongate portion is arranged to co-operate with a correspondingly-shaped portion of the mouthpiece 20'. The elongate portion 121 provides protection for the valve stem when the mouthpiece 20' has been removed. In addition, the main body 5' is provided with one or more slots 122 in an upper region for interaction with corresponding parts of the fixing collar 3'.

The detachable mouthpiece 20' is provided with one or more fixtures 120 for attaching the mouthpiece 20' to the main body 5'. In particular, a push-fit attachment is provided by the mouthpiece 20' having one or more internal armatures 120 each comprising a notch 123 which co-operates with a corresponding groove (not shown) located in the internal surface of the main body 5' on assembly. Accordingly, it is very simple to change the mouthpiece of the dispensing apparatus, if desired. The mouthpiece 20' is also provided with a block (not shown) for receipt of the valve stem 22 of a loaded container 10 or the elongate portion 121. A dust cap (not shown) may be placed over the open distal end of the mouthpiece 20'.

Figure 10:
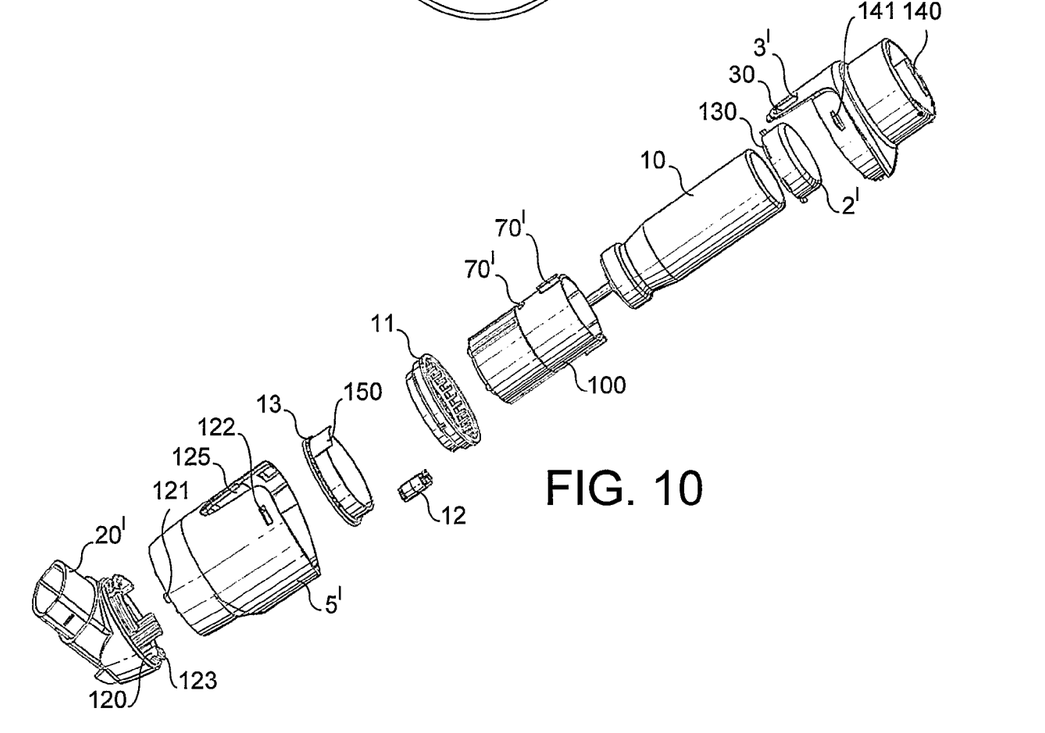
FIG. 10 is an exploded view of the dispensing apparatus of FIG. 9, together with a container.
Figure 11:
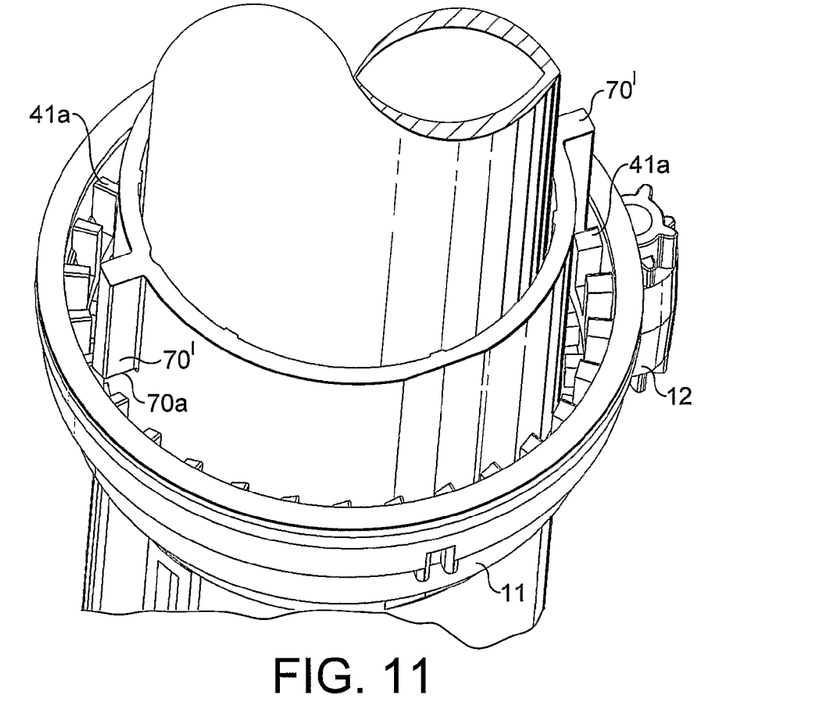
FIG. 11 is a perspective view of various internal features of the dispensing apparatus of FIG. 9.
Figure 13:
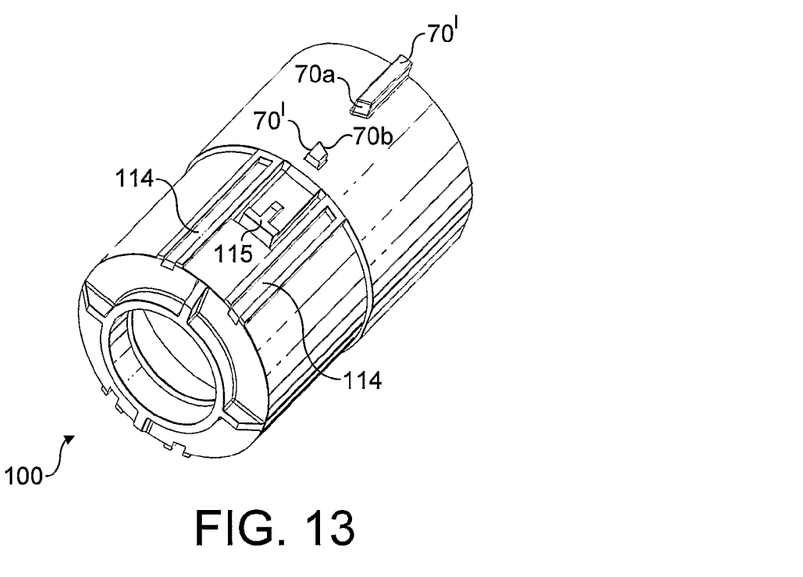
FIG. 13 is a perspective view of a sleeve for use in the dispensing apparatus of FIG. 9.
Figure 14:
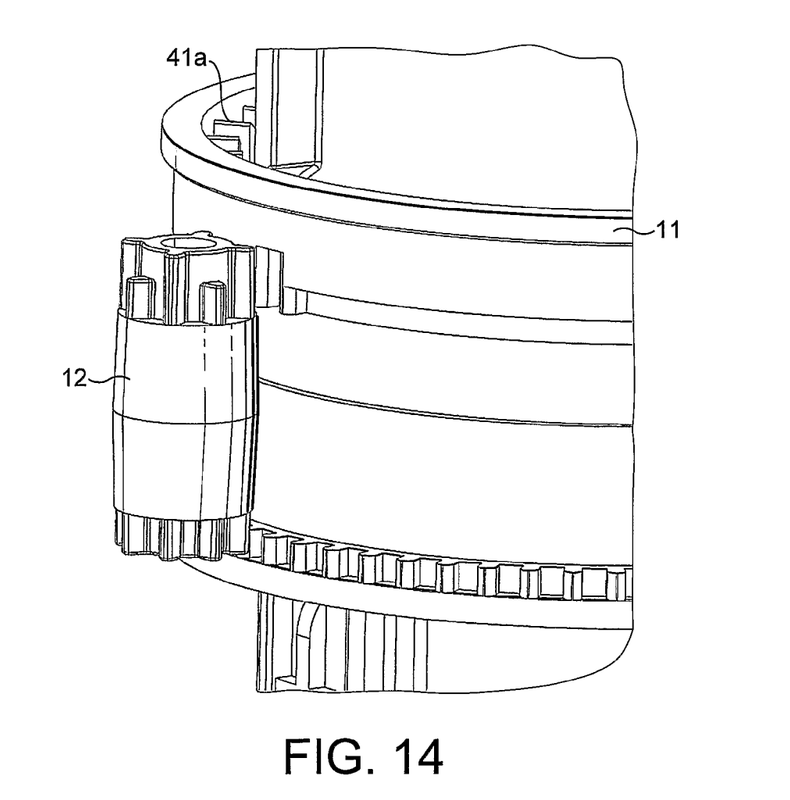
FIG. 14 is a perspective view of first and second number rings and a cog of the dispensing apparatus of FIG. 9.
Figure 15:
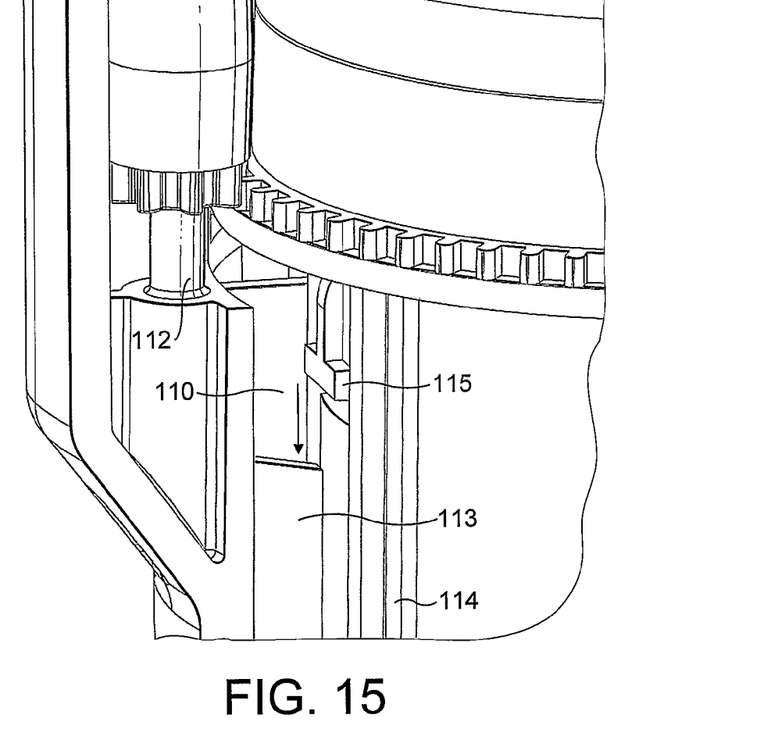
FIG. 15 is a partial-cross-sectional view of the dispensing apparatus of FIG. 9 and shows internal features of the body of the dispensing apparatus.

As shown in FIGS. 10 and 13, the sleeve 100 comprises an open-ended cylinder having an upper end which can receive a container 10 to be located in the dispensing apparatus 1' and a lower end which has a reduced diameter opening through which the valve stem 22 of a container 10, located within the sleeve 100 may protrude from but through which the body of the container 10 cannot pass. The sleeve 100 is further provided with a number of projections 70' on its exterior having angled abutment surfaces 70a,70b for co-operation with angled abutment surfaces 41 of the first number ring 11, as described below. Preferably, two sets of two projections 70' are provided on opposite outsides of the sleeve 100. Each set comprises two spaced-apart opposing angled abutment surfaces 70a,70b which are angled in a manner as mirror images of each other. The two sets are oriented in the same direction to provide only one direction of rotation of the number ring 11. Additionally, the sleeve 100 is provided with slots 114 into which the internal projections 110 of the main body 5' can slide during location of the sleeve 100, within the main body 5' and actuation of the dispensing apparatus. The sleeve 100 is also provided with a resilient member 115, in the form of a sprung cantilevered catch, for interaction with the static abutment surface 113 of the main body 5', as will be described below.

As shown in FIG. 10, the cap 2' fits over the upper end of the container 10, opposite the metering valve. The cap 2' is provided with a plurality of external flange portions 130, for interaction with the fixing collar 3'.

The fixing collar 3' is provided with one or more notches 141 for locating in the one or more slots 122 of the main body 5', so as to provide an improved push-fit attachment of the fixing collar 3' to the main body 5'. The fixing collar 3' is provided with internal flange portions 140, such that, the external flange portions 130 of the cap 2' interact with the internal flange portions 140 to retain the cap 2' and, therefore, the container 10, within the main body 5' when closed. The fixing collar 3' is provided with a clear portion 30, or one or more apertures 30 through which portions provided with markings of number rings 11,13 are visible. Preferably, the fixing collar 3' is provided with a projection 124 at the end of which is provided the clear portion 30 or one or more apertures 30. This projection 124 extends into the region of the main body 5' into a correspondingly-shaped hole 125. This arrangement provides the clear portion 30 or the one or more apertures 30 at a position in the region of the main body 5' which allows viewing of the markings on the number rings 11,13.

The fixing collar 3', in combination with the cap 2', provides a closure to the upper end of the main body 5', remote from the mouthpiece 20'. In addition, the internal parts of the dispensing apparatus, for example, the number rings 11,13, the cog 12', the sleeve 100, and the container are held within the main body 5' by the fixing collar 3' and the cap 2'.

Figure 16:
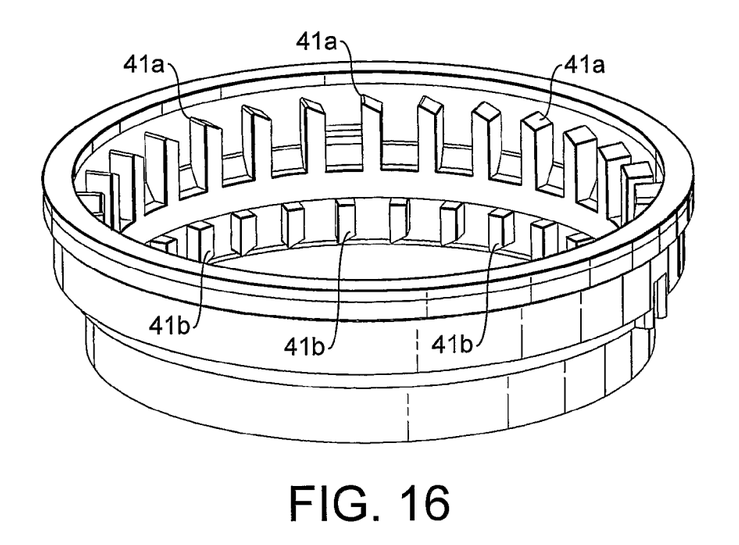
FIG. 16 is a perspective view of a first number ring having two different diameter portions, for use with the dispensing apparatus of FIG. 9.

In this alternative embodiment, the first number ring 11 may be provided with two rows of angled abutment surfaces 41 located on two different diameter portions of that number ring. The angled abutment surfaces 41 of a larger diameter portion are indicated by reference 41a and those of a smaller diameter by reference 41b, as shown in FIG. 16, in particular.

The second number ring 13 is provided with an extended portion 150 which is positioned to enable covering of the markings on the first number ring 11 when a container locatable in the housing is empty. Advantageously, the extended portion 150 provides a clear indication to a user that the dispensing apparatus has provided its full-quota of dispensations.

Figure 12:
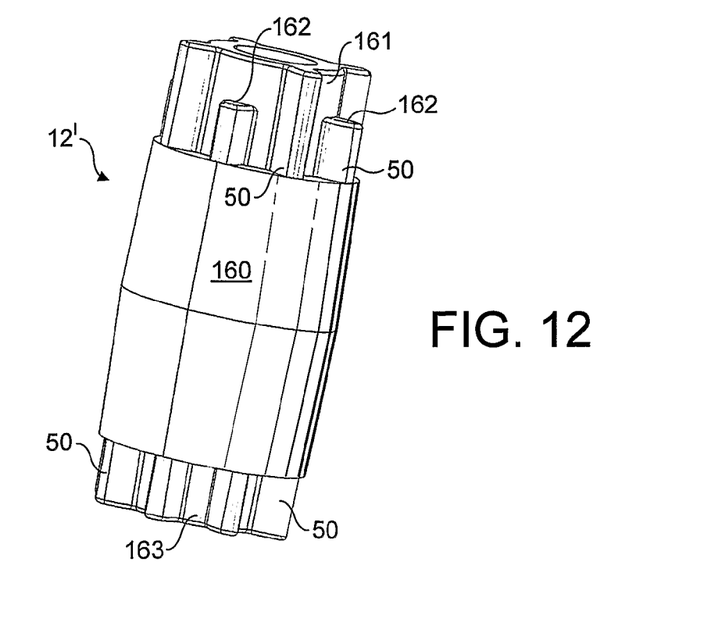
FIG. 12 is a perspective view of a cog for use in the dispensing apparatus of FIG. 9.

The cog 12', as shown in FIG. 12 in particular, is provided with one or more teeth 50' separated by a non-toothed spacer 160, such that, a first end 161 of the cog 12', including one or more teeth 162 of reduced height, may interact with the first annular member 11 and a second end of the cog 163, which is not provided with one or more teeth of reduced height, may interact with the second annular member 13. The one or more teeth 162 having reduced height are, typically, half the height of the non-reduced-height teeth, which non-reduced-height teeth extend from the spacer 160 to the face of the first end 161 of the cog 12'. Most preferably, cog 12' is provided with a reduced-height tooth 162 interspaced between each pair of non-reduced-height teeth.

In use, this alternative embodiment of dispensing apparatus is actuated in a similar manner to the first embodiment of dispensing apparatus. Additionally, the slots 114 of the sleeve 100 slide down the internal projections 110 of the main body 5' during actuation and, thus, guiding the valve stem 22 against the abutment (not shown) within the elongate portion 121. In addition, the resilient member 115 of the sleeve 100 abuts the static abutment surface 113 of the main body 5'. Such abutment provides increased resistance to actuation above the normal resistance provided by the reaction force of the valve stem 22 which must be overcome before actuation can occur. Advantageously, the resistance requires a minimum actuation force to a be applied before actuation of the dispensing apparatus occurs—which helps to standardise the dosage of pharmaceutical dispensed.

The present arrangement provides partial-incremental rotations of the first number ring 11. When the dispensing apparatus is actuated—by a longitudinal down-stroke of the cap 2' and the container 10—a first angled abutment surface 70a of each set of portions 70' interacts with at least one angled abutment surface 41a of the larger diameter portion of the first number ring 11 to provide a partial incremental rotation of the first number ring 11. Further, during a corresponding reciprocal up-stroke of the cap 2' and the container 10, a second angled abutment surface 70b of each set of portions 70' interacts with at least one angled abutment surface 41b of the smaller diameter portion of first number ring 11 to provide a second and final partial-incremental rotation of the first number ring 11. Therefore, an augmented or decreased number is indicated to a user by a two-step rotation of the first number ring 11 upon actuation of the dispensing apparatus 1'.

As mentioned in relation to the previous embodiment, the number rings 11,13 surround or are located around the container 1', when the container 10 is loaded in the dispensing apparatus 1'. Further, the sleeve 100 and the container 10 are slidable within the main body 5' and pass through the holes/apertures of the number rings 11,13.

Whilst in the specific example details of the invention are discussed, it will of course be understood that minor variations in features are still considered to be covered by the same inventive concept.

In an alternative embodiment, the dispensing apparatus may comprise, say, three or more number rings: a first number ring for 'units', a second for 'tens' and a third for 'hundreds'. Further cogs may be provided. Subsequent number rings for 'thousands' and so on may also be added. The second and subsequent number rings are rotated by an arrangement as described herein (by a cog rotated by a previous number ring), whereby ten incremental rotations of the previous number ring—as started originally on the 'units' number ring by actuation of the apparatus—causes an incremental rotation of the subsequent number ring.

The invention claimed is:

1. A dispensing apparatus comprising a housing containing a dosage counter comprising first and second annular members, each mounted rotationally, the housing being suitable for receiving, in use, a container containing a product for dispensation, the container being locatable to pass within holes/apertures of the first and second annular members characterised in that the apparatus further comprises a cog, the axis of rotation of the cog being offset from the axes of rotation of the first and second annular members and the axis of rotation of the cog being located outside the first and second annular members whereupon each actuation of the apparatus causes the first annular member to incrementally rotate which, after a predetermined number of actuations of the apparatus, causes the cog to rotate, the rotation of the cog causing the second annular member to incrementally rotate.

2. A dispensing apparatus as claimed in claim 1, wherein a longitudinal actuation force applied, in use, to the container is converted to a rotational force applied to the first annular member by way of co-operating formations having angled abutment surfaces.

3. A dispensing apparatus as claimed in claim 2, wherein the first annular member is provided with angled abutment surfaces.

4. A dispensing apparatus as claimed in claim 2, wherein the dispensing apparatus further comprises a cap or sleeve, for surrounding at least part of a container locatable in the dispensing apparatus, the cap or sleeve being provided with angled abutment surfaces.

5. A dispensing apparatus as claimed in claim 3, wherein the first annular member, and/or the cap or sleeve is/are provided with one or more sets of angled abutment surfaces at different diameters.

6. A dispensing apparatus as claimed in claim 5, wherein respective sets of angled abutment surfaces of the first annular member, and the cap or sleeve co-operate, in use, to provide an incremental rotation of the first annular member upon a longitudinal actuation of the sleeve or cap.

7. A dispensing apparatus as claimed in claim 5, wherein a first set of co-operating portions of the first annular member, and the sleeve or cap co-operate to provide a partial-incremental rotation of the annular member upon a down-stroke longitudinal actuation of the dispensing apparatus and a second set of co-operating portions of the first annular member, and the sleeve or cap co-operate to provide a second and final partial-incremental rotation of the first annular member upon a reciprocal up-stroke longitudinal actuation of the dispensing apparatus.

8. A dispensing apparatus as claimed in claim 1, wherein the first annular member is provided with means for affecting rotation of the cog.

9. A dispensing apparatus as claimed in claim 8, wherein, when the rotation means of the first annular member is a notch or protrusion positioned on an outer edge of the first annular member, the notch or protrusion is capable of interacting with a correspondingly-shaped portion of the cog.

10. A dispensing apparatus as claimed in claim 9, wherein the rotation means of the first annular member is a notch, the cog is turned by way of a tooth catching the notch of the first annular member as the member rotates upon actuation of the apparatus.

11. A dispensing apparatus as claimed in claim 9, wherein, the rotation means of the first annular member is a protrusion and the cog has a correspondingly-shaped notch.

12. A dispensing apparatus as claimed in claim 8, wherein three rotation means are positioned on the outer edge of the first annular member.

13. A dispensing apparatus as claimed in claim 8, wherein respective rotation means are positioned ten increments of rotation apart.

14. A dispensing apparatus as claimed in claim 1, wherein each respective part of the cog which interacts with the first and second annular members has a different number of teeth.

15. A dispensing apparatus as claimed in claim 14, wherein the ratio of teeth on respective parts of the cog which interact with the first and second annular member is 1:2.

16. A dispensing apparatus as claimed in claim 1, wherein the cog is made of resilient material.

17. A dispensing apparatus as claimed in claim 1, wherein the cog is resiliently positioned against an outer edge of the first annular member.

18. A dispensing apparatus as claimed in claim 1, wherein the first and/or second annular members are provided with one or more sets of markings indicative of the amount or number of doses of product dispensed from, or remaining in, a container received within the apparatus.

19. A dispensing apparatus as claimed in claim 18, wherein the sets of markings are numbering or variations of colour and/or tone.

20. A dispensing apparatus as claimed in claim 19, wherein numbering on the first annular member ranges from 0 to 9 and that of the second annular member from 00 to 20, so that when both are seen in combination, a three-figure number is shown.

21. A dispensing apparatus as claimed in claim 19, wherein each actuation of the apparatus causes the value of numbering to decrease or augment by a value of one.

22. A dispensing apparatus as claimed in claim 18, wherein the second annular member is provided with an extended portion which is positioned on the second annular member so as to cover the markings of the first annular member when a container locatable in the housing is empty.

23. A dispensing apparatus as claimed in claim 1 comprising means for locking-out operation of a container located in the housing.

24. A dispensing apparatus as claimed in claim 1, wherein the dispensing apparatus is provided with a mouthpiece which is detachable from the housing.

25. A dispensing apparatus as claimed in claim 4, wherein a portion of the sleeve or cap and a portion of the housing are adapted to provide resistance to actuation of the dispensing apparatus.

26. A dispensing apparatus as claimed in claim 25, wherein the portion of the sleeve or cap is a resilient member.

27. A dispensing apparatus as claimed in claim 25, wherein the portion of the housing is a static abutment surface which, during use, is temporarily abutable by the portion of the sleeve or cap.

28. A dispensing apparatus as claimed in claim 1, wherein the apparatus further comprises third and subsequent annular members, a cog being provided for each additional annular member.

29. A dispensing apparatus as claimed in claim 28, wherein a predetermined number of rotations of the second or previous annular member causes an incremental rotation of the third or subsequent annular member.

30. A dispensing apparatus as claimed in claim 1, wherein the cog comprises a hub, with a pivot hole situated in the centre thereof, and a plurality of teeth outwardly-extending from the centre of the cog, the cog being rotatable about a longitudinal axis through the hole, wherein one or more teeth have a reduced height in the direction of the longitudinal axis, in that upper and lower edges of the tooth are not inline with both upper and lower faces of the cog.

31. A dispensing apparatus as claimed in claim 30, wherein the one or more teeth having a reduced height are half the height of the other teeth.

32. A dispensing apparatus as claimed in claim 30, wherein the cog comprises a reduced-height tooth interspaced between each pair of non-reduced-height teeth.

33. A dispensing apparatus as claimed in claim 30, wherein all the reduced-height teeth are positioned at either an upper or lower edge of the cog.

34. A dispensing apparatus as claimed in 30, wherein portions of the one or more teeth are separated by a non-toothed spacer, such that, in use, a first end of the cog, including one or more teeth of reduced height, interacts with the first annular member and a second end of the cog, which is not provided with one or more teeth of reduced height, interacts with the second annular member.

35. A dispensing apparatus as claimed in claim 34, wherein the one or more teeth having reduced height are half the height of the non-reduced-height teeth, which non-reduced-height teeth extend from the spacer to the face of the first end of the cog.

36. A dispensing apparatus as claimed in claim 34, wherein the cog comprises a reduced-height tooth interspaced between each pair of non-reduced-height teeth.

37. A dispensing apparatus as claimed in claim 1 further comprising a container located in the housing of the dispensing apparatus.

38. A dispensing apparatus as claimed in claim 37, wherein the annular members are located around the container.

39. A dispensing apparatus as claimed in claim 37, wherein the container is pressurised.

* * * * *